United States Patent [19]

Sweeney

[11] Patent Number: 5,057,636

[45] Date of Patent: Oct. 15, 1991

[54] PROCESS FOR RECOVERING N-HEXENES FROM A MIXTURE OF $C_6$ OLEFIN ISOMERS BY OLIGOMERIZING THE BRANCHED-CHAIN $C_6$ OLEFIN ISOMERS IN THE MIXTURE USING A MODERATE STRENGTH ACID CATLYST

[75] Inventor: William A. Sweeney, Larkspur, Calif.

[73] Assignee: Chevron Research and Technology Company, San Francisco, Calif.

[21] Appl. No.: 542,299

[22] Filed: Jun. 22, 1990

[51] Int. Cl.$^5$ ............................................... C07C 1/00
[52] U.S. Cl. .................................. 585/324; 585/510; 585/520; 585/639; 585/643; 585/644; 585/648; 585/653
[58] Field of Search ............. 585/324, 328, 329, 326, 585/639, 640, 648, 510, 520, 643, 644, 653; 568/697

[56] References Cited

U.S. PATENT DOCUMENTS

| | | | |
|---|---|---|---|
| 3,283,027 | 11/1966 | Lundeen et al. | 260/682 |
| 3,600,455 | 8/1971 | Dean | 260/682 |
| 4,110,410 | 8/1978 | Ryu | 585/510 |
| 4,234,752 | 11/1980 | Wa et al. | 585/640 |
| 4,270,015 | 5/1981 | Knifton | 585/324 |
| 4,283,305 | 8/1981 | Chauvin et al. | 252/431 |
| 4,316,851 | 2/1982 | Pennec et al. | 260/408 |
| 4,366,087 | 12/1982 | Pennec et al. | 252/431 |
| 4,398,049 | 8/1983 | Pennec et al. | 385/512 |
| 4,490,567 | 12/1984 | Drake | 585/324 |

FOREIGN PATENT DOCUMENTS

| | | |
|---|---|---|
| 0222356 | 5/1987 | European Pat. Off. . |
| 0150832 | 2/1988 | European Pat. Off. . |
| 1233020 | 5/1971 | United Kingdom . |

OTHER PUBLICATIONS

Lundeen, et al., *JORG Chem.*, vol. 32, 1967, pp. 3386-3389.

Davis, *American Chemical Society*, vol. 18, No. 3, 1979, pp. 191-198.

Che, et al., *Elsevier Science Publishers B.V.*, Amsterdam, 1985, pp. 309-318.

Benedek et al., *Oil & Gas Journal*, Apr. 28, 1990, pp. 77-83.

*Primary Examiner*—Curtis R. Davis
*Attorney, Agent, or Firm*—Richard J. Sheridan; Tom G. DeJonghe

[57] ABSTRACT

Processes are disclosed for recovering n-hexenes from a mixture comprising n-hexenes and at least one branched-chain $C_6$ olefin isomer by oligomerizing the branched-chain $C_6$ olefin isomers, but not the n-hexenes, and recovering the n-hexenes from the resulting mixture.

23 Claims, No Drawings

PROCESS FOR RECOVERING N-HEXENES FROM A MIXTURE OF $C_6$ OLEFIN ISOMERS BY OLIGOMERIZING THE BRANCHED-CHAIN $C_6$ OLEFIN ISOMERS IN THE MIXTURE USING A MODERATE STRENGTH ACID CATLYST

BACKGROUND OF THE INVENTION

1. Field of the Invention

The present invention relates to a process for recovering n-hexenes from a mixture of $C_6$ olefin isomers and a process for producing 1-hexene from a mixture of $C_6$ olefin isomers.

2. Description of the Prior Art

Compounds having a terminal double bond (hereinafter referred to as "terminal olefins" or "α-olefins") are very useful industrially as raw materials for heat-resistant polymers, comonomers for the production of polyolefins, starting materials for detergents and so forth. The terminal olefin 1-hexene is especially valuable for many uses such as dimerization to dodecenes which are suitable for making biodegradable detergents, using it as a feed for the OXO reaction to make relatively linear $C_7$ alcohols, and as a comonomer in making linear low density polyethylene.

A potential source of 1-hexene is a mixture of n-hexenes which contains 1-hexene, cis and trans 2-hexene, and cis and trans 3-hexene. These n-hexenes can be found at appreciable levels (over about 10% by weight) in certain mixtures of $C_6$ olefin isomers prepared, for example, by the dimerization of propylene. Generally, propylene dimers prepared using acid catalysis do not contain appreciable amounts of n-hexenes, and are, thus, not suitable as a source of n-hexenes. Propylene dimers prepared by transition metal catalysis usually do contain appreciable amounts of n-hexenes, and are useful as a source of n-hexenes. Mixtures of propylene dimers made via nickel or cobalt catalysis are particularly suitable. Depending upon the reaction conditions and the form of the catalyst, the n-hexene content in mixtures of propylene dimers prepared via nickel or cobalt catalysis can vary from zero to 75% by weight. The remaining $C_6$ olefin isomers in these mixtures of propylene dimers are branched-chain $C_6$ olefins. These branched-chain $C_6$ olefins are difficult to separate from the n-hexenes because at least some of them have boiling points very close to those of the n-hexenes.

There are processes known for separating branched-chain $C_4$ and $C_5$ olefins from their straight chain isomers by extraction with dilute (about 65%) sulfuric acid. However, this extraction approach is not desirable for mixtures of $C_6$ olefin isomers because of the poorer extraction equilibrium with $C_6$ olefins, and the requirement of working with a large volume of corrosive sulfuric acid.

Thus, there exists a need for a process of recovering n-hexenes from a mixture of $C_6$ olefin isomers containing n-hexenes and branched-chain $C_6$ olefin isomers.

While, as noted above, mixtures of $C_6$ olefin isomers can be made which contain appreciable amounts of n-hexenes, the amount of 1-hexene in these mixtures is normally low. For example, thermodynamic equilibration of n-hexenes produces a mixture containing only about 2–4% 1-hexene. While it is possible to separate the 1-hexene from the other n-hexenes in these mixtures, due to the very low levels of 1-hexene, such a procedure would be uneconomical. Thus, there exists a need for a method by which the amount of 1-hexene in these n-hexene mixtures can be substantially increased.

A known method for producing terminal olefins, such as 1-hexene, is to dehydrate a 2-alcohol, i.e., a compound of the formula

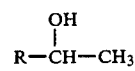

where R is a hydrocarbyl group. For example, U.S. Pat. No. 3,283,027, issued Nov. 1, 1966 to Lundeen et al., discloses the dehydration of 2-alcohols to terminal olefins (also known as "α-olefins") using a catalyst which is a thorium, scandium, yttrium or rare earth oxide. While this dehydration reaction can produce an α-olefin and/or a 2-olefin, the Lundeen et al. product is said to be 90% or more α-olefin.

U S. Pat. No. 3,600,455, issued Aug. 17, 1971 to Dean, discloses a process for producing the terminal olefin 4-methylpentene-1 by dehydrating 4-methyl pentanol-1 or 4-methyl pentanol-2 by passing it over an alkalized alumina catalyst.

U.S. Pat. No. 4,234,752, issued Nov. 18, 1980 to Wu et al., discloses the dehydration of $C_{2-20}$ alcohols in the presence of gamma-alumina (which may be base-treated) employing an inert carrier gas to produce an olefin. The process is said to minimize isomerization which can convert desired products to undesired products. For example, according to Wu et al., 3-methyl-1-butanol can be dehydrated by this process to produce 3-methyl-1-butene having a 97.7 wt. % purity.

U.S. Pat. No. 4,490,567, issued Dec. 25, 1984 to Drake, discloses a process for the selective dehydration of 2-alcohols to α-olefins using a catalyst which is (1) at least one catalytic metal oxide on a low surface area aluminum oxide-containing support, or (2) a mixture of thorium oxide and cerium oxide on a base-treated aluminum oxide-containing support. Also described is a process for obtaining high purity 4-methyl-1-pentene by the dehydration of 4-methyl-2-pentanol followed by disproportionation with ethylene.

European Patent Specification Publication No. 0150832, published Nov. 2, 1988, discloses a process for preparing α-olefins by dehydrating 2-alcohols using a high purity (i.e., substantially free of silicon and titanium) zirconium oxide catalyst, and European Patent Specification Publication No. 0222356, published May 20, 1987, discloses the dehydration of 2-alcohols to α-olefins using a zirconia catalyst which has been treated with an alkaline solution.

Lundeen and Hoozer, "Selective Catalytic Dehydration. Thoria-Catalyzed Dehydration of Alcohols", J. Org, Chem., 32, pp. 3386–3389 (1967) discloses that the thoria-catalyzed dehydration of secondary 2-alcohols is selective for α-olefins, and that the amount of ketone by-product is low, and Davis, "Catalytic Conversion of Alcohols. 11. Influence of Preparation and Pretreatment on the Selectivity of Zirconia", Ind. Eng. Chem. Prod. Res. Dev., Vol. 18, No. 3, pp. 181–198 (1979) discloses that a zirconia catalyst is similar to thoria for both the dehydration and α-olefin selectivity in the conversion of 2-alcohols to olefins.

Other methods of preparing α-olefins are also known. For example, British Patent Specification No. 1,233,020, published May 26, 1971, discloses a method for making 4-methylpentene-1 by subjecting a mixture of acetone and isobutyraldehyde to conditions under which acetone undergoes condensation both with itself to form diacetone alcohol and with isobutyraldehyde to form the acetone/isobutyraldehyde condensate methyl 2-methyl 3-hydroxy butyl ketone, subjecting the mixed condensates to conditions under which they undergo dehydration to the corresponding olefinically unsaturated ketones, hydrogenating these ketones to saturated alcohols and dehydrating these saturated alcohols over alkalized alumina to form a mixture of 4-methylpentenes-1 and -2 and a mixture of methyl hexenes.

A process for recovering n-hexenes from a mixture of n-hexenes and branched-chain $C_6$ olefin isomers has now been discovered, as well as a process for producing 1-hexene from a mixture of $C_6$ olefin isomers.

SUMMARY OF THE INVENTION

In accordance with the present invention, there is provided a process for the recovery of n-hexenes from a mixture comprising n-hexenes and at least one branched-chain $C_6$ olefin isomer, said process comprising:

A. contacting a mixture comprising n-hexenes and at least one branched-chain $C_6$ olefin isomer with a moderate strength acid catalyst capable of oligomerizing the branched-chain $C_6$ olefin but not the n-hexenes under reaction conditions and for a time sufficient to cause oligomerization of the branched-chain $C_6$ olefin; and B. recovering the n-hexenes from the product of step A.

In accordance with the present invention, there is further provided a process for the recovery of n-hexenes from a mixture comprising n-hexenes, at least one branched-chain $C_6$ olefin isomer having its branch at the double bond, and at least one branched-chain $C_6$ olefin having its branch at a point other than at the double bond, said process comprising:

A. contacting a mixture comprising n-hexenes, at least one branched-chain $C_6$ olefin isomer having its branch at the double bond, and at least one branched-chain $C_6$ olefin having its branch at a point other than at the double bond with a moderate strength acid catalyst capable of oligomerizing the branched-chain $C_6$ olefin having its branch at the double bond, but not the n-hexenes under reaction conditions and for a time sufficient to cause oligomerization of the branched-chain $C_6$ olefin having its branch at the double bond, but not the n-hexenes; and B. recovering the n-hexenes from the product of step A.

In accordance with the present invention there is also provided a process for making 1-hexene comprising:

A. contacting a mixture comprising 2-hexene and at least one branched-chain $C_6$ olefin isomer with a moderate strength acid catalyst capable of oligomerizing the branched-chain $C_6$ olefin but not the 2-hexene under reaction conditions and for a time sufficient to cause oligomerization of the branched-chain $C_6$ olefin;

B. removing the oligomers from the product of step A;

C. reacting the remainder of the product of step A with an electrophilic compound containing reactive hydrogen under conditions which permit the electrophilic compound containing reactive hydrogen to add to carbon-carbon double bonds; and D. cracking the product of step C to produce a mixture of $C_6$ olefins containing 1-hexene.

In accordance with the present invention, there is also provided a process for making 1-hexene comprising:

A. contacting a mixture comprising 2-hexene and at least one branched-chain $C_6$ olefin isomer with a moderate strength acid catalyst capable of oligomerizing the branched-chain $C_6$ olefin but not the n-hexenes under reaction conditions and for a time sufficient to cause oligomerization of the branched-chain $C_6$ olefin;

B. removing the oligomers from the product of step A;

C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;

D. hydrolyzing the product of step C to produce of mixture of $C_6$ alcohols; and E. cracking the product of step D to produce a mixture of $C_6$ olefins containing 1-hexene.

The present invention further provides a process for making 1-hexene comprising:

A. contacting a mixture comprising 2-hexene and at least one branched-chain $C_6$ olefin isomer with a moderate strength acid catalyst capable of oligomerizing the branched-chain $C_6$ olefin but not the 2-hexene under reaction conditions and for a time sufficient to cause oligomerization of the branched-chain $C_6$ olefin;

B. removing the oligomers from the product of step A;

C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;

D. when the electrophilic reactant employed in step C is a hydrolyzable electrophilic compound containing reactive hydrogen, hydrolyzing the product of step C to form alcohols;

E. converting the alcohols produced to alkyl xanthates; and

F. cracking the product of step E to produce a mixture of $C_6$ olefins containing 1-hexene.

In accordance with the present invention there is also provided a process for making 1-hexene comprising:

A. contacting a mixture comprising 2-hexane, at least one branched-chain $C_6$ olefin isomer having its branch at the double bond, and at least one branched-chain $C_6$ olefin having its branch at a point other than at the double bond with a moderate strength acid catalyst capable of oligomerizing the branched-chain $C_6$ olefin having its branch at the double bond, but not the 2-hexene under reaction conditions and for a time sufficient to cause oligomerization of the branched-chain $C_6$ olefin having its branch at the double bond, but not the 2-hexene;

B. removing the oligomers from the product of step A;

C. reacting the remainder of the product of step A with an electrophilic compound containing reactive hydrogen under conditions which permit the electrophilic compound containing reactive hydrogen to add to carbon-carbon double bonds; and D. cracking the product of step C to produce a mixture of $C_6$ olefins containing 1-hexene.

In accordance with the present invention, there is also provided a process for making 1-hexene comprising:

A. contacting a mixture comprising 2-hexene, at least one branched-chain C₆ olefin isomer having its branch at the double bond, and at least one branched-chain C₆ olefin having its branch at a point other than at the double bond with a moderate strength acid catalyst capable of oligomerizing the branched-chain C₆ olefin having its branch at the double bond, but not the 2-hexene under reaction conditions and for a time sufficient to cause oligomerization of the branched-chain C₆ olefin having its branch at the double bond, but not the 2-hexene;

B. removing the oligomers from the product of step A;

C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;

D. hydrolyzing the product of step C to produce of mixture of C₆ alcohols; and

E. cracking the product of step D to produce a mixture of C₆ olefins containing 1-hexene.

The present invention further provides a process for making 1-hexene comprising:

A. contacting a mixture comprising 2-hexene, at least one branched-chain C₆ olefin isomer having its branch at the double bond, and at least one branched-chain C₆ olefin having its branch at a point other than at the double bond with a moderate strength acid catalyst capable of oligomerizing the branched-chain C₆ olefin having its branch at the double bond, but not the 2-hexene under reaction conditions and for a time sufficient to cause oligomerization of the branched-chain C₆ olefin having its branch at the double bond, but not the 2-hexene;

B. removing the oligomers from the product of step A;

C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;

D. when the electrophilic reactant employed in step C is a hydrolyzable electrophilic compound containing reactive hydrogen, hydrolyzing the product of step C to form alcohols;

E. converting the alcohols produced to alkyl xanthates; and

F. cracking the product of step E to produce a mixture of C₆ olefins containing 1-hexene.

DETAILED DESCRIPTION OF PREFERRED EMBODIMENTS

The starting material employed in the processes of the present invention is a mixture of C₆ olefin isomers comprising n-hexenes and at least one branched-chain C₆ olefin. As used herein, the term "branched-chain C₆ olefin" refers to olefins having 6 carbon atoms and a branch in the molecule. These branched-chain C₆ olefins can have their branch either at the double bond or at some point other than at the double bond. Examples of branched-chain C₆ olefins which have the branch at the double bond are the following compounds:

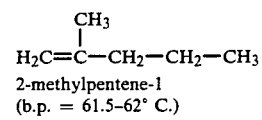
2-methylpentene-1
(b.p. = 61.5–62° C.)

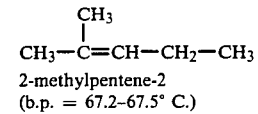
2-methylpentene-2
(b.p. = 67.2–67.5° C.)

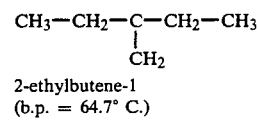
2-ethylbutene-1
(b.p. = 64.7° C.)

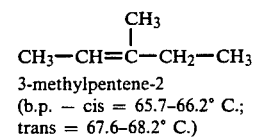
3-methylpentene-2
(b.p. — cis = 65.7–66.2° C.; trans = 67.6–68.2° C.)

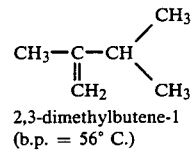
2,3-dimethylbutene-1
(b.p. = 56° C.)

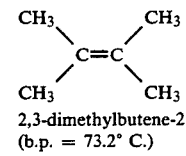
2,3-dimethylbutene-2
(b.p. = 73.2° C.)

Examples of branched-chain C₆ olefins which have their branch at a point other than at the double bond are the following compounds:

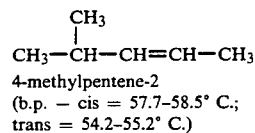
4-methylpentene-2
(b.p. — cis = 57.7–58.5° C.; trans = 54.2–55.2° C.)

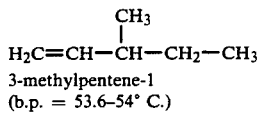
3-methylpentene-1
(b.p. = 53.6–54° C.)

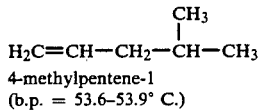
4-methylpentene-1
(b.p. = 53.6–53.9° C.)

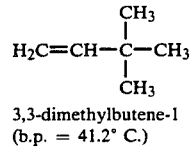
3,3-dimethylbutene-1
(b.p. = 41.2° C.)

The term branched-chain C₆ olefin includes both cis and trans isomers, where applicable.

The boiling points of several of the above branched-chain C₆ olefins are very close to the boiling points of n-hexenes (which have boiling points in the 63°–68° C.

range) making them very difficult, if not impossible, to separate from n-hexenes by distillation techniques.

The branched-chain $C_6$ olefins having their branch at the double bond are very reactive, and will oligomerize quite readily. While the branched-chain $C_6$ olefins which have their branch at a point other than at the double bond are not as reactive, depending upon the catalyst and reaction conditions selected, some (or all) of these compounds may oligomerize as well.

The starting material also contains n-hexenes, i.e., 1-, 2-, and/or 3-hexene. When the process of this invention is used to produce 1-hexene, the starting material must contain some amount of 2-hexene.

The source of the starting mixture is not critical. It could come from various cracking operations such as fluid catalytic cracking or steam cracking. A convenient source is the mixture of propylene dimers made by metal-catalyzed processes such as those described in Chem. Rev. 1986, p. 353. Particularly suitable are the nickel catalyzed processes such as the Dimersol process. This process was developed by Institut Francaise du Petrole and involves the catalyzed, liquid phase dimerization of propylene.

The Dimersol process is described in Benedek et al., Oil & Gas Journal., Apr. 28, 1980, pp. 77-83, which is incorporated by reference herein in its entirety. The process is also generally described in U.S. Pat. No. 4,283,305 (issued Aug. 11, 1981 to Chauvin et al.); U.S. Pat. No. 4,316,851 (issued Feb. 23, 1982 to Le Pennec et al.); U.S. Pat. No. 4,366,087 (issued Dec. 28, 1982 to Le Pennec et al.); and U.S. Pat. No. 4,398,049 (issued Aug. 9, 1983 to Le Pennec et al.), each of which is incorporated by reference herein in its entirety.

The product of the dimerization of propylene by the Dimersol process is often referred to as "Dimate" and, as disclosed in the aforementioned Benedek et al. article, contains high octane isohexenes and small quantities of trimers and higher molecular weight olefins. The product contains 1-, 2- and 3-hexene; 2-methylpentene-2; 4-methylpentene-2 and 2,3-dimethylbutene-2. If desired, the 4-methylpentene-2 may be separated from the Dimate product by distillation prior to its use in the process of the present invention.

In the first step of the process of this invention, i.e., the oligomerization step, careful control of conditions is required in order that as much of the branched-chain $C_6$ olefins are oligomerized as is possible without allowing the n-hexenes to react to an appreciable extent with themselves or with the branched-chain olefins. The main controlling parameter is the strength of the acid catalyst. The strength of the catalyst may vary somewhat, but in general it must be sufficiently strong to cause oligomerization of substantially all of the branched-chain $C_6$ olefin while leaving the n-hexenes as a group essentially intact. (Some double isomerization of the n-hexenes may occur, but this does not detract significantly from the overall process.) A moderated sulfonic acid catalyst such as Amberlyst 15, available from the Rohm and Haas Co., is suitable. As used herein, the term "moderate" or "moderated" means that the activity of the pure acid has been lowered by the presence of water, sodium ions, or the like which lower the acidity of the catalyst but do not react appreciably with the branched-chain $C_6$ olefin or n-hexenes. Other moderated solid or liquid acid catalysts, such as aqueous sulfuric acid, are also suitable.

Nonselective oligomerization of olefins with dry macroreticular sulfonic acid ion exchange resin catalysts has been described by N. M. Bortnick in U.S. Pat. No. 3,037,052, issued May 29, 1962. To use this type of catalyst in the present invention it is moderated by the incorporation of at least about 0.5 mole of water per mole of sulfonic acid groups; preferably about 1 mole of water per mole of sulfonic acid groups. However, up to about 3 to 4 moles of water per mole of sulfonic acid can be used. At this level, practically all of the sulfonic acid groups are dissociated from each other. (See G. Zundel, "Hydration and Intermolecular Interaction," Academic Press, New York, 1969 and A. R. Pitochelli, "Ion exchange Catalysis and Matrix Effects," Rohm and Haas Co., Philadelphia, 1988.) More water can be present, but is less desirable due to an overall loss of activity.

Amberlyst 15 catalyst contains about 4.7 meq. of acid groups per gram on a dry basis. The desired water content for this catalyst for use in the process of this invention, then, is at least about 4% water (0.5 mole of water per mole of sulfonic acid groups); preferably about 8% (1 mole of water per mole of sulfonic acid); and up to about 25% (4 moles of water per mole of sulfonic acid).

As an alternative to adding water to moderate the strength of the resin catalyst, less than a stoichiometric amount of alkali or alkaline earth cations can be added, as described in U.S. Pat. No. 3,678,099, issued July 18, 1972 to J. D. Kemp. That patent discloses that Amberlyst 15 acid strength is reduced to 0.2 from 2.4 meq. of sulfonic acid per gram of catalyst.

It is generally desired in the present invention to decrease the catalytic activity of the acid catalyst only to the point where substantially all, e.g., greater than about 80%, of the n-hexenes are left intact while the branched-chain $C_6$ olefins oligomerize. In this way, the activity for this oligomerization is kept high.

The other important parameter which should be controlled during the oligomerization step is temperature. Moderate temperatures in the 50° to 150° C. range are preferred, with the higher temperatures in this range being used when the acid strength of the catalyst is lower.

The second step of the process of the present invention is removal of the oligomerized compounds from the oligomerization reaction product. This is typically accomplished via distillation techniques. In this way, the n-hexenes can be recovered in high purity. Preferably, fractional distillation techniques are employed. If some branched-chain $C_6$ olefin does remain in the oligomerization product, the purity of the recovered n-hexenes will depend on the degree of fractionation employed. It is, however, highly desirable to assure that as much 2-methylpentene-2 as possible has been oligomerized, since it boils at the same point as the n-hexenes.

In another embodiment of the present invention, the oligomerization conditions in the first step of the process can be moderated to the point where some, but not all of the branched-chain $C_6$ olefins present in the starting mixture are oligomerized. For example, branched-chain $C_6$ olefins which are branched at the double bond (such as 2-methylpentene-2) oligomerize at a faster rate than do the branched-chain $C_6$ olefins which have their branch at a point other than at the double bond (such as 4-methylpentene-2). Therefore, the reaction conditions (i.e., catalyst acid strength, time and temperature) can be moderated to the point where the branched-chain $C_6$ olefins having their branch at the double bond will oligomerize, but some of those having their branch elsewhere (and the n-hexenes) will not. Since the branched-chain $C_6$ olefins which have their branches at a point other than at the double bond can generally be separated from n-hexenes simply by distillation but those with there branches at the double bond cannot, this embodiment permits the use of relatively mild oligomerization conditions, yet at the same time providing a method of removing those branched-chain $C_6$ olefins which are the most difficult to separate from the n-hexenes.

When the n-hexenes have been recovered in substantially pure form the resulting mixture of n-hexenes can be used to prepare 1-hexene. The n-hexenes are reacted with an electrophilic compound containing reactive hydrogen. Examples of suitable electrophilic compounds containing reactive hydrogen include, but are not limited to, water, carboxylic acids (such as formic acid, acetic acid, trimethylacetic acid and dimethylbutyric acids), and sulfuric acid. The electrophilic compound containing reactive hydrogen is reacted with the n-hexenes, which normally include 1-, 2- and 3-hexene, under conditions which permit it to add to the carbon-carbon double bond in the n-hexenes. The resulting reaction product comprises a mixture of 2- and 3-hexyl isomers

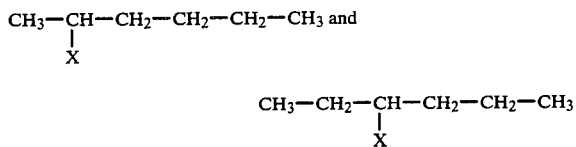

where X is the negative group (e.g., —OH, —OOCCH$_3$ or HSO$^-_4$) from the electrophilic compound containing reactive hydrogen.

The conditions for the addition of the electrophilic compound to the olefins are well known in the art. Generally, acid catalysis is useful. This can often be provided by the electrophilic compound itself.

The electrophilic compounds containing reactive hydrogen useful in this invention fall into two general categories. The first category comprises compounds which, after they have added to the double bonds in the hexene isomers, can be removed directly by cracking the 2- and 3-hexyl isomers. Compounds which fall into this category include water and carboxylic acids, such as formic acid, acetic acid, trimethylacetic acid and dimethylbutyric acids. (In some cases, it may be desirable, though not necessary, to hydrolyze the electrophilic compounds in this first category, such as the carboxylic acids, to alcohols prior to cracking.) The second category of electrophilic compounds containing reactive hydrogen comprises compounds which add to the double bonds in the hexenes, but which are not readily removed from the 2- and 3-hexyl isomers by cracking, e.g., sulfuric acid. When this second category of compounds is used, the 2- and 3-hexyl isomers produced are subjected to an intermediate step, such as hydrolysis, to convert the negative group from the electrophilic compound containing reactive hydrogen (i.e., X in the above formulas) to a group, such as hydroxyl, which can be readily removed from the 2- and 3-hexyl isomers by cracking.

When the electrophilic compound containing reactive hydrogen employed is water, the 2- and 3-hexyl isomers produced will contain hydroxyl groups in the 2 and 3 positions, i.e., the product will contain 2-hexanol and 3-hexanol. Also, some of the electrophilic compounds containing reactive hydrogen which are useful in this invention can be hydrolyzed to a hydroxyl after addition to the double bond. These alcohols can be converted to xanthate groups, i.e., "2-xanthate" and "3-xanthate" compounds prepared, respectively, from 2-hexanol and 3-hexanol, which can then be removed via cracking. This conversion of alcohol to xanthate can be accomplished by reacting the alcohol with carbon disulfide (CS$_2$) in the presence of base (e.g., NaOH), followed by alkylation with, e.g., methyl iodide.

As stated above, the product of the reaction of the n-hexenes and electrophilic compound containing reactive hydrogen is a mixture of 2- and 3-hexyl isomers. This mixture may be used in the subsequent cracking procedure, or, alternatively, the 2-isomers (2-hexanol, 2-xanthate, etc.) may be separated from the mixture of 2- and 3-hexyl isomers and only the 2-isomer subjected to cracking. By separating the 2-isomer in this manner, the concentration of 1-hexene in the product of the cracking procedure will be maximized.

Once the 2- and 3-hexyl isomers produced by reaction of the n-hexenes with the electrophilic compound containing reactive hydrogen contains a group which is readily removed by cracking, the mixture of 2- and 3-hexyl isomers (or the 2-isomer alone) is cracked to produce a significantly higher quantity of 1-hexene than was present in the mixture of $C_6$ olefin isomers used as the starting material. Depending upon the particular readily removable group which is present on the 2- and 3-hexyl isomers, removal of the group may be accomplished by simple thermal cracking or by a cracking procedure which utilizes a catalyst. For example, when acetic acid is used as the electrophilic compound containing reactive hydrogen, thermal cracking may be used. When the 2- and 3-hexyl isomers are 2- and 3-hexyl alcohols, the cracking is preferably conducted in the presence of a mildly basic metal oxide catalyst. Water is removed from each molecules to produce a mixture of 1-hexene, 2-hexene and 3-hexene which has a quantity of 1-hexene in it which is greater than the quantity of 1-hexene in the mixture of $C_6$ olefin isomers used as the starting material.

The materials useful as cracking catalysts should not be acidic or strongly basic. Acid catalysts can isomerize the $\alpha$-olefin product to internal olefins, which is undesirable. If a strongly basic catalyst is used, appreciable dehydrogenation of the alcohol would occur, which is undesirable. Thus, suitable catalysts are mildly basic metal oxides which do not cause appreciable dehydrogenation of the alcohol and which exhibit selectivity for the production of $\alpha$-olefins. While not specific to the production of 1-hexene, this general type of catalyst is discussed in an article by Burtron H. Davis entitled "Alcohol Conversion Selectivity as a Measure of the Base Strength of Metal Oxide Catalysts" in Che et al., *Adsorption and Catalysis on Oxide Surfaces* (1985); which article is incorporated by reference herein in its entirety. Examples of mildly basic metal oxides suitable as catalysts in this invention include the oxides of Y, Zr, La, In, Ce, Pr, Nd, Sm, En, Dy, Ho, Yb and Th.

It has been found that hydrous zirconium oxide prepared by a particular technique is an especially suitable catalyst. This catalyst is prepared by precipitating/digesting soluble ZrO(NO$_3$)$_2$ at high pH above room temperature (e.g., about 50°–75° C.), washing the resulting product thoroughly with both aqueous ammonia and water and drying exhaustively (e.g., at 80° C. or higher under vacuum for at least 16 hours). Before use, the catalyst is calcined at about 350°–650° C. This catalyst provides excellent conversion of 2-hexanol to olefin as well as excellent selectivity for α-olefin in the product.

When the mixture of $C_6$ olefin isomers used for the starting material is derived from the Dimersol process, the above-described process can be depicted by the following general reaction scheme. This general reaction scheme is illustrative only and is not intended to limit the present invention in any way.

STEP 1

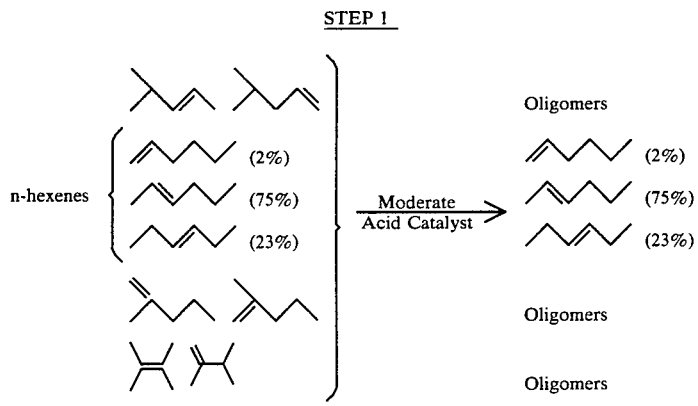

In the above Step 1, the percentages in parentheses refer to the relative amounts of 1-, 2- and 3-hexene, i.e., the weight percentages of 1-, 2- and 3-hexene based on the total weight of 1-, 2- and 3-hexene.

The oligomers (and preferably any branched-chain olefins remaining after oligomerization) are separated from the product of Step 1 by distillation, and the next step in the general reaction scheme would typically be:

STEP 2

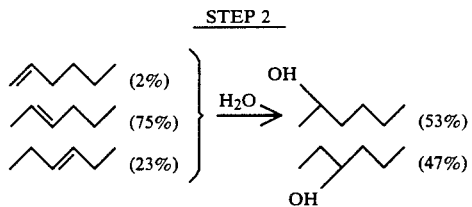

The yield of 2-hydroxyhexane (which ultimately can yield 1-hexene) in Step 2 (53 wt. % of the total product) is not substantially higher than the yield which would be expected for random addition of the water to the double bonds, i.e., about 50% of the alcohols produced would be expected to be 2-hydroxy hexane if random addition occurred. However, it has been found that the amount of 2-hydroxyhexane in this product can be increased significantly above this random level by using an electrophilic compound containing reactive hydrogen other than water. For instance, if acetic acid is used, the product contains about 63% of the 2-isomer and 37% of the 3-isomer. Using sulfuric acid as the electrophilic compound containing reactive hydrogen yields a product containing about 73% of the 2-isomer and 27% of the 3-isomer. The use of "bulky" acids, such as trimethylacetic acid or dimethylbutyric acids, should likewise increase the amount of 2-isomer in the product.

The product of Step 2 can next be "cracked" to a mixture of n-hexenes. The resulting mixture contains a quantity of 1-hexene substantially higher than the quantity present in the starting material used in Step 1.

STEP 3

The desired product from the above reaction sequence is, of course, 1-hexene. However, it is not necessary that the 1-hexene be separated from the 2- and 3-hexene in order for it to be useful. For example, the mixture of 1-, 2- and 3-hexene can be used as a starting material for the copolymerization of 1-hexene and ethylene. Since 2- and 3-hexene will not react to copolymerize with the ethylene, they act simply as an inert diluent which can be recovered following the copolymerization of the 1-hexene and ethylene. Thus, the copolymerization also serves as a means of separating the 2- and 3-hexene from the 1-hexene.

Should it be desirable to separate the 1-hexene from the mixture of 1-, 2- and 3-hexene prior to its use, this can be accomplished by techniques such as distillation or adsorption which are well known in the art.

The processes of the present invention for producing 1-hexene may be conducted either as a batch process or in a continuous manner. It is generally preferable to conduct the process in a continuous manner. The product of the cracking step will generally contain some quantity of 2- and/or 3-hexenes, and possibly some compounds which were not cracked and still contain the electrophilic group of the electrophilic compound containing reactive hydrogen (e.g., alcohols). Thus, the processes of this invention are advantageously conducted by recovering the desired product, 1-hexene, from the product of the cracking step, and recycling any remaining n-hexenes and uncracked compounds to be used as a portion of the feed for the reaction with the electrophilic compound containing active hydrogen. This may be accomplished by recycling these compounds to a point in the process where they will become part of the original starting material, e.g., to a point before reaction with the electrophilic compound containing reactive hydrogen. In this way the amount of 1-hexene produced from a given mixture of $C_6$ olefin isomers is maximized. This recycling technique may also be used to generate some 2-hexene (from which the 1-hexene is made) in a starting material which contains, e.g., 3-hexene as the only n-hexene.

One of the principle advantages of the present invention is that it provides a process whereby 1-hexene can be produced in commercially acceptable amounts. In effect, the process of this invention starts with a mixture of n-hexenes which is low in 1-hexene and raises the quantity of 1-hexene in the mixture by converting some of the 2- and 3-hexene in the mixture to 1-hexene. For example, the mixture of propylene dimers typically resulting from the Dimersol process contains about 75% 2-hexene, about 23% 3-hexene and only about 2% 1-hexene, all percentages being by weight based on the total weight of the 1-, 2- and 3-hexene. By practicing the present invention, the amount of 1-hexene can be raised to about 50% or higher.

The present invention is further illustrated by the following examples in which all percentages are by weight unless otherwise stated.

EXAMPLE 1

A mixture of n-hexenes and branched-chain $C_6$ olefins produced commercially by the Dimersol process was used as the starting material. This mixture was about 92 wt. % $C_6$ olefins and about 8 wt. % $C_9+$ olefins. The following $C_6$ olefins were present in the following amounts:

| $C_6$ Olefin | Approx. Wt. %[d] |
|---|---|
| 1-hexene | 0.5 |
| 2-hexene[a] | 17.9 |
| 3-hexene[a] | 5.6 |
| 2,3-dimethylbutene-1[b] | 2.5 |
| 2-methylpentene-1[b] | 5.0 |
| 2-methylpentene-2[b] | 35.2 |
| 2,3-dimethylbutene-2[b] | 4.4 |
| 4-methylpentene-1[c] | 1.3 |
| 4-methylpentene-2[a,c] | 27.6 |

[a]includes cis and trans isomers
[b]branched-chain $C_6$ olefin with the branch at the double bond
[c]branched-chain $C_6$ olefin with the branch at a point other than the double bond
[d]based on total weight of $C_6$ olefins only This mixture was contacted with Amberlyst 15 sulfonic acid catalyst which was moderated by the presence of 10% water. A relatively low reaction temperature of 75° C. was used, and the reaction was continued for about 10 hours. Analysis of the product showed that the following compounds were present in the amounts shown in Table I below.

TABLE I

| Compound Type | Analysis By Gas Chromatography | Analysis By Distillation |
|---|---|---|
| $C_6$ olefins | 24[e] | 20 |
| $C_9$ compounds | 6 | 8 |
| $C_{12}$ compounds | 65 | 58 |
| $C_{15}+$ compounds | 5 | 15 |

[e]Numbers are wt. % of whole product.

This product was then fractionally distilled. As seen from Table II below, most of the unreacted $C_6$ olefins were n-hexenes, which indicates that substantially all of the branched-chain $C_6$ olefins had oligomerized. A heart-cut of the $C_6$ olefins was analyzed as 88 wt. % n-hexene. The amount of n-hexenes in the product approximated the amount of n-hexenes in the original starting material. From the analyses it was estimated that the 2-methylpentene-2 in the starting material was 99% converted to oligomers, and the 4-methylpentene-2 was 90% converted.

TABLE II

| | | DISTILLATION[h] CUTS | | | | |
|---|---|---|---|---|---|---|
| | | Composition, Wt. % | | | | |
| Cut | B.P. (°C.) | Branched $C_6$ Olefins[f] | n-Hexenes | Branched $C_6$ Olefins[g] | $C_9$ | $C_{12}$ | $C_{15}+$ |
| 1 | 62–65.5 | 39 | 58 | 3 | — | — | — |
| 4–6 | 68–69 | 5 | 88 | 6 | — | — | — |
| 9 | 132–140 | — | 1 | — | 99 | — | — |
| 12–27 | 185–203 | — | — | — | — | 100 | — |
| 29 | 220–239 | — | — | — | — | 34 | 66 |

[f]4-methylpentene-2 and 4-methylpentene-1
[g]2-methylpentene-1; 2-methylpentene-2; 2,3-dimethylbutene-1 and 2,3-dimethylbutene-2
[h]Penn State packing; 5/1 reflux ratio; 3.2% cuts The following examples illustrate the preparation of 1-hexene from a mixture comprising n-hexenes.

EXAMPLE 2

This example illustrates the hydration of n-hexenes using sulfuric acid.

50 Grams of a mixture containing 1% 1-hexene, 71% 2-hexene and 28% 3-hexene was added to 93 grams of 78% sulfuric acid at 15° C. over 10 minutes while stirring and cooling. Then 60 grams of concentrated (96–97%) sulfuric acid was added over 15 minutes while keeping the temperature of the mixture at 15° C. The resulting mixture was digested at 24° C. for 1-hour. Then 288 grams of water was added at 15° C. and the intermediate sulfates which formed were hydrolyzed by heating at 80° C. for 3 hours. The resulting product contained about 70% 2-hexanol and 30% 3-hexanol. The results of this experiment and three other similar experiments are summarized below in Table III.

TABLE III

| | n-HEXENE HYDRATION | | | | | | | | |
|---|---|---|---|---|---|---|---|---|---|
| | Olefin Addition[i] | | $H_2SO_4$ Addition[j] | | Digestion | | Water Addition[k] | Hydrolysis | | Products[l] | |
| Run No. | Temp. °C. | Time, Min. | Temp. °C. | Time, Min. | Temp. °C. | Time, Min. | Temp. °C. | Temp. °C. | Time, Min. | Color, Gardner | GC Percent 2-Hexanol in Hexanols |
| 1 | 15 | 10 | 15 | 15 | 24 | 60 | 15 | 80 | 180 | 7 | 71 |
| 2 | 30 | 10 | 30 | 15 | 30 | 60 | 30 | 80 | 180 | 7.5 | 72 |
| 3 | 5 | 10 | 5 | 15 | 5 | 120 | 15 | 80 | 180 | 4 | 74 |

TABLE III-continued n-HEXENE HYDRATION

| Run No. | Olefin Addition[i] Temp. °C. | Olefin Addition[i] Time, Min. | H$_2$SO$_4$ Addition[j] Temp. °C. | H$_2$SO$_4$ Addition[j] Time, Min. | Digestion Temp. °C. | Digestion Time, Min. | Water Addition[k] Temp. °C. | Hydrolysis Temp. °C. | Hydrolysis Time, Min. | Products[l] Color, Gardner | Products[l] GC Percent 2-Hexanol in Hexanols |
|---|---|---|---|---|---|---|---|---|---|---|---|
| 4 | 15 | 45 | 15 | 60 | 24 | 60 | 15 | 80 | 180 | 4.5 | 73 |

[i] 50 g (0.595 moles) n-hexene added to 93 g of 78 H$_2$SO$_4$ (0.74 moles)
[j] 60 g (0.59 moles) conc. H$_2$SO$_4$
[k] 288 g water
[l] Organic layer washed with base and dried The hydration procedure described in this example can be used in the present invention as Step 2 in the above-described general reaction scheme.

EXAMPLE 3

A mixture of n-hexenes was prepared containing 92.4% n-hexenes and 7.6% branched hexenes. This mixture was hydrated by a procedure similar to that of Example 2 except that the starting sulfuric acid strength was about 77% and the stronger acid (137 grams) added subsequently was only about 82%. The conversion (about 75%) and alcohol isomer distribution (73% 2-hexanol and 27% 3-hexanol) were about the same as in Example 2. The minor amount of branched hexenes in the feed mostly formed oligomers which were easily separated by distillation.

The hydrated hexenes prepared above were distilled. The results are shown in Table IV below. The 2- and 3-hexanols were partially separated with the last cuts being up to about 97% 2-hexanol.

As with the procedure described in Example 2, the hydration procedure described in this example can be used in the practice of the present invention as Step 2 in the above-described general reaction scheme.

converted to hexenes and a small amount of hexanones. Selectivity to olefin was about 94% and 1-hexene selectivity was about 75%. 1-Hexene can be recovered in pure form from the resulting product by careful fractional distillation.

The procedure described in this example can be used in the practice of this invention as Step 3 in the above-described general reaction scheme.

What is claimed is:

1. A process for the recovery of n-hexenes from a mixture comprising n-hexenes and at least one branched-chain C$_6$ olefin isomer, said process comprising:
   A. contacting a mixture comprising n-hexenes and at least one branched-chain C$_6$ olefin isomer with a moderate strength acid catalyst capable of oligomerizing the branched-chain C$_6$ olefin but not the n-hexenes under reaction conditions and for a time sufficient to cause oligomerization of the branched-chain C$_6$ olefin; and
   B. recovering the n-hexenes from the product of step A.

2. A process for the recovery of n-hexenes from a mixture comprising n-hexenes, at least one branched-

TABLE IV

DISTILLATION OF HEXANOLS FROM DIMATE[m]

| Cut | Boiling Point, °C. | Composition, CG Area % n-Hexene | "Branched Hexene" | "Branched Hexanol" | 3-Hexanol | 2-Hexanol | Oligomer |
|---|---|---|---|---|---|---|---|
| 1 | 62–64 | 90.4 | 8.2 | — | 0.5 | 0.9 | — |
| 4 | 68–70 | 91.2 | 6.4 | 0.1 | 0.8 | 1.5 | — |
| 8 | 138 | — | — | 1.2 | 43.6 | 55.2 | — |
| 13 | 139– | — | — | 0.2 | 41.4 | 58.2 | — |
| 18 | 139+ | — | — | — | 38 | 62 | — |
| 20–36 | 139–140.5 | | | — | 26.9 | 73.1 | — |
| 37–43 | 140.5–141 | | | | 9.7 | 90.3 | — |
| 46 | 197–199 | | | | 0.1 | 1.2 | 98.7 (C$_{12}$) |
| Bottoms | 253+ | | | | | | 100 (C$_{18}$+) |

[m] 3-Ft Spinning Band, Atm. Pressure, 20/1 reflux ratio, 2% Cuts

EXAMPLE 4

This example illustrates the dehydration of hexanols to produce 1-hexene.

A wide range of catalysts was tested to identify catalysts that would produce 1-hexene in high selectivities from the dehydration of 2-hexanol. One catalyst which performed well was a zirconia powder sold by Magnesium Elektron Inc. known as "SC101". This powder was pelletized and crushed to 10–30 mesh particles. 4 Grams were packed in a 0.5 in. diameter quartz tube and calcined in nitrogen at 550° C. for 4 hours. The feed alcohol was passed at 0.5 ml/hr over the catalyst at 300° C. in a nitrogen flow of 3 ml/min. Two blends of 2- and 3-hexanols from Table IV (cuts 20–36 and cuts 37–43) were dehydrated by this procedure. In both cases the 2-hexanol component of the blend was about 40 to 60% chain C$_6$ olefin isomer having its branch at the double bond, and at least one branched-chain C$_6$ olefin having its branch at a point other than at the double bond, said process comprising:
   A. contacting a mixture comprising n-hexenes, at least one branched-chain C$_6$ olefin isomer having its branch at the double bond, and at least one branched-chain C$_6$ olefin having its branch at a point other than at the double bond with a moderate strength acid catalyst capable of oligomerizing the branched-chain C$_6$ olefin having its branch at the double bond, but not the n-hexenes under reaction conditions and for a time sufficient to cause oligomerization of the branched-chain C$_6$ olefin having its branch at the double bond, but not the n-hexenes; and B. recovering the n-hexenes from the product of step A.

3. A process for making 1-hexene comprising:
A. contacting a mixture comprising 2-hexene and at least one branched-chain $C_6$ olefin isomer with a moderate strength acid catalyst capable of oligomerizing the branched-chain $C_6$ olefin but not the 2-hexene under reaction conditions and for a time sufficient to cause oligomerization of the branched-chain $C_6$ olefin;
B. removing the oligomers from the product of step A;
C. reacting the remainder of the product of step A with an electrophilic compound containing reactive hydrogen under conditions which permit the electrophilic compound containing reactive hydrogen to add to carbon-carbon double bonds; and
D. cracking the product of step C to produce a mixture of $C_6$ olefins containing 1-hexene.

4. The process of claim 3 wherein the electrophilic compound containing reactive hydrogen is selected from water and carboxylic acids.

5. The process of claim 3 further comprising separating the 1-hexene from the product of the cracking step and recycling the remainder of said product to form a portion of the material used to react with the electrophilic compound containing reactive hydrogen.

6. A process for making 1-hexene comprising:
A. contacting a mixture comprising 2-hexene and at least one branched-chain $C_6$ olefin isomer with a moderate strength acid catalyst capable of oligomerizing the branched-chain $C_6$ olefin but not the n-hexenes under reaction conditions and for a time sufficient to cause oligomerization of the branched-chain $C_6$ olefin;
B. removing the oligomers from the product of step A;
C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;
D. hydrolyzing the product of step C to produce of mixture of $C_6$ alcohols; and
E. cracking the product of step D to produce a mixture of $C_6$ olefins containing 1-hexene.

7. The process of claim 6 further comprising separating the 1-hexene from the product of the cracking step and recycling the remainder of said product to form a portion of the material used to react with the electrophilic compound.

8. The process of claim 4 wherein the electrophilic compound is sulfuric acid or a carboxylic acid.

9. A process for making 1-hexene comprising:
A. contacting a mixture comprising 2-hexene and at least one branched-chain $C_6$ olefin isomer with a moderate strength acid catalyst capable of oligomerizing the branched-chain $C_6$ olefin but not the 2-hexene under reaction conditions and for a time sufficient to cause oligomerization of the branched-chain $C_6$ olefin;
B. removing the oligomers from the product of step A;
C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;
D. when the electrophilic reactant employed in step C is a hydrolyzable electrophilic compound containing reactive hydrogen, hydrolyzing the product of Step C to form alcohols;
E. converting the alcohols produced to alkyl xanthates; and
F. cracking the product of step E to produce a mixture of $C_6$ olefins containing 1-hexene.

10. The process of claim 9 wherein the electrophilic reactant is selected from water, sulfuric acid, and carboxylic acids.

11. The process of claim 9 further comprising separating the 1-hexene from the product of the cracking step and recycling the remainder of said product to form a portion of the material used to react with the electrophilic reactant.

12. A process for making 1-hexene comprising:
A. contacting a mixture comprising 2-hexene, at least one branched-chain $C_6$ olefin isomer having its branch at the double bond, and at least one branched-chain $C_6$ olefin having its branch at a point other than at the double bond with a moderate strength acid catalyst capable of oligomerizing the branched-chain $C_6$ olefin having its branch at the double bond, but not the 2-hexene under reaction conditions and for a time sufficient to cause oligomerization of the branched-chain $C_6$ olefin having its branch at the double bond, but not the 2-hexene;
B. removing the oligomers from the product of step A;
C. reacting the remainder of the product of step A with an electrophilic compound containing reactive hydrogen under conditions which permit the electrophilic compound containing reactive hydrogen to add to carbon-carbon double bonds; and
D. cracking the product of step C to produce a mixture of $C_6$ olefins containing 1-hexene.

13. The process of claim 12 wherein the electrophilic compound containing reactive hydrogen is selected from water and carboxylic acids.

14. The process of claim 12 further comprising separating the 1-hexene from the product of the cracking step and recycling the remainder of said product to form a portion of the material used to react with the electrophilic compound containing reactive hydrogen.

15. A process for making 1-hexene comprising:
A. contacting a mixture comprising 2-hexene, at least one branched-chain $C_6$ olefin isomer having its branch at the double bond, and at least one branched-chain $C_6$ olefin having its branch at a point other than at the double bond with a moderate strength acid catalyst capable of oligomerizing the branched-chain $C_6$ olefin having its branch at the double bond, but not the 2-hexene under reaction conditions and for a time sufficient to cause oligomerization of the branched-chain $C_6$ olefin having its branch at the double bond, but not the 2-hexene;
B. removing the oligomers from the product of step A;
C. reacting the remainder of the product of step A with an electrophilic compound containing reactive hydrogen under conditions which permit said electrophilic compound to add to carbon-carbon double bonds, said electrophilic compound being hydrolyzable to an alcohol after addition to the carbon-carbon double bond;

D. hydrolyzing the product of step C to produce of mixture of $C_6$ alcohols; and E. cracking the product of step D to produce a mixture of $C_6$ olefins containing 1-hexene.

16. The process of claim 15 further comprising separating the 1-hexene from the product of the cracking step and recycling the remainder of said product to form a portion of the material used to react with the electrophilic compound.

17. The process of claim 15 wherein the electrophilic compound is sulfuric acid or a carboxylic acid.

18. A process for making 1-hexene comprising:

A. contacting a mixture comprising 2-hexene, at least one branched-chain $C_6$ olefin isomer having its branch at the double bond, and at least one branched-chain $C_6$ olefin having its branch at a point other than at the double bond with a moderate strength acid catalyst capable of oligomerizing the branched-chain $C_6$ olefin having its branch at the double bond, but not the 2-hexene under reaction conditions and for a time sufficient to cause oligomerization of the branched-chain $C_6$ olefin having its branch at the double bond, but not the 2-hexene;

B. removing the oligomers from the product of step A;

C. reacting the remainder of the product of step A with an electrophilic reactant selected from the group consisting of water and a hydrolyzable electrophilic compound containing reactive hydrogen under conditions which permit said electrophilic reactant to add to carbon-carbon double bonds;

D. when the electrophilic reactant employed in step C is a hydrolyzable electrophilic compound containing reactive hydrogen, hydrolyzing the product of step C to form alcohols;

E. converting the alcohols produced to alkyl xanthates; and

F. cracking the product of step E to produce a mixture of $C_6$ olefins containing 1-hexene.

19. The process of claim 18 further comprising separating the 1-hexene from the product of the cracking step and recycling the remainder of said product to form a portion of the material used to react with the electrophilic reactant.

20. The process of claim 18 wherein the electrophilic reactant is selected from water, sulfuric acid, and carboxylic acids.

21. The process of claim 3, 4, 6, 9, 12, 13, 15 or 18 wherein the cracking is conducted in the presence of a mildly basic metal oxide catalyst capable of selectively producing α-olefins.

22. The process of claim 1, 2, 3, 4, 5, 6, 7, 9, 11, 12, 13, 14, 15, 16, 18 or 19 wherein the moderate strength acid catalyst is a sulfonic acid ion exchange resin.

23. The process of claim 21 wherein the moderate strength acid catalyst is a sulfonic acid ion exchange resin.

* * * * *